United States Patent [19]

Miller et al.

[11] 4,321,040
[45] Mar. 23, 1982

[54] ENDODONTIC INSTRUMENT

[75] Inventors: Alan Miller, New City; Edward E. Schweizer, Katonah, both of N.Y.; John E. Campanello, Caldwell, N.J.

[73] Assignee: Ipco Corporation, White Plains, N.Y.

[21] Appl. No.: 214,665

[22] Filed: Dec. 9, 1980

[51] Int. Cl.³ ............................................... A01C 5/02
[52] U.S. Cl. .................................................... 433/102
[58] Field of Search .................. 433/102, 141; 145/61, 145/61 A, 61 B

[56] References Cited

U.S. PATENT DOCUMENTS

| 811,390 | 1/1906 | Foreman | 145/61 B |
| 3,119,423 | 1/1964 | Weick | 145/61 F |
| 4,260,379 | 4/1981 | Groves | 433/102 |

*Primary Examiner*—Robert Peshock
*Attorney, Agent, or Firm*—Friedman, Goodman & Teitelbaum

[57] ABSTRACT

An endodontic instrument is described which includes a handle from which extends an endo blade. The handle includes an elongated sleeve member formed of resilient material which surrounds a core member secured within the sleeve member. The core member has a longitudinal body portion radially spaced from the inner walls of the sleeve to define therebetween a flexure space for accommodating the deformation of the sleeve member upon gripping of the handle during use of the instrument. Preferably, the sleeve member is provided with gripping ribs thereon.

18 Claims, 15 Drawing Figures

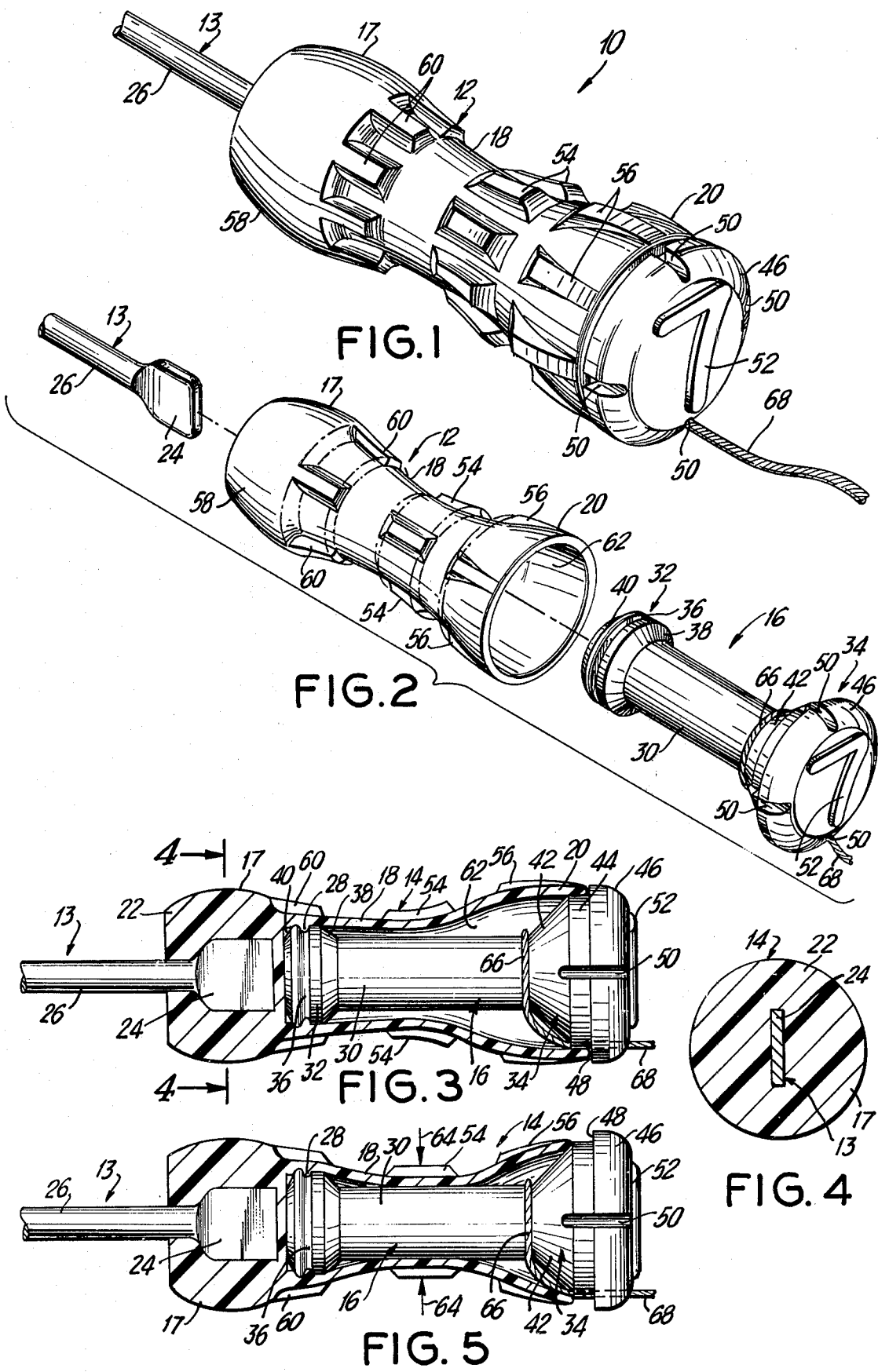

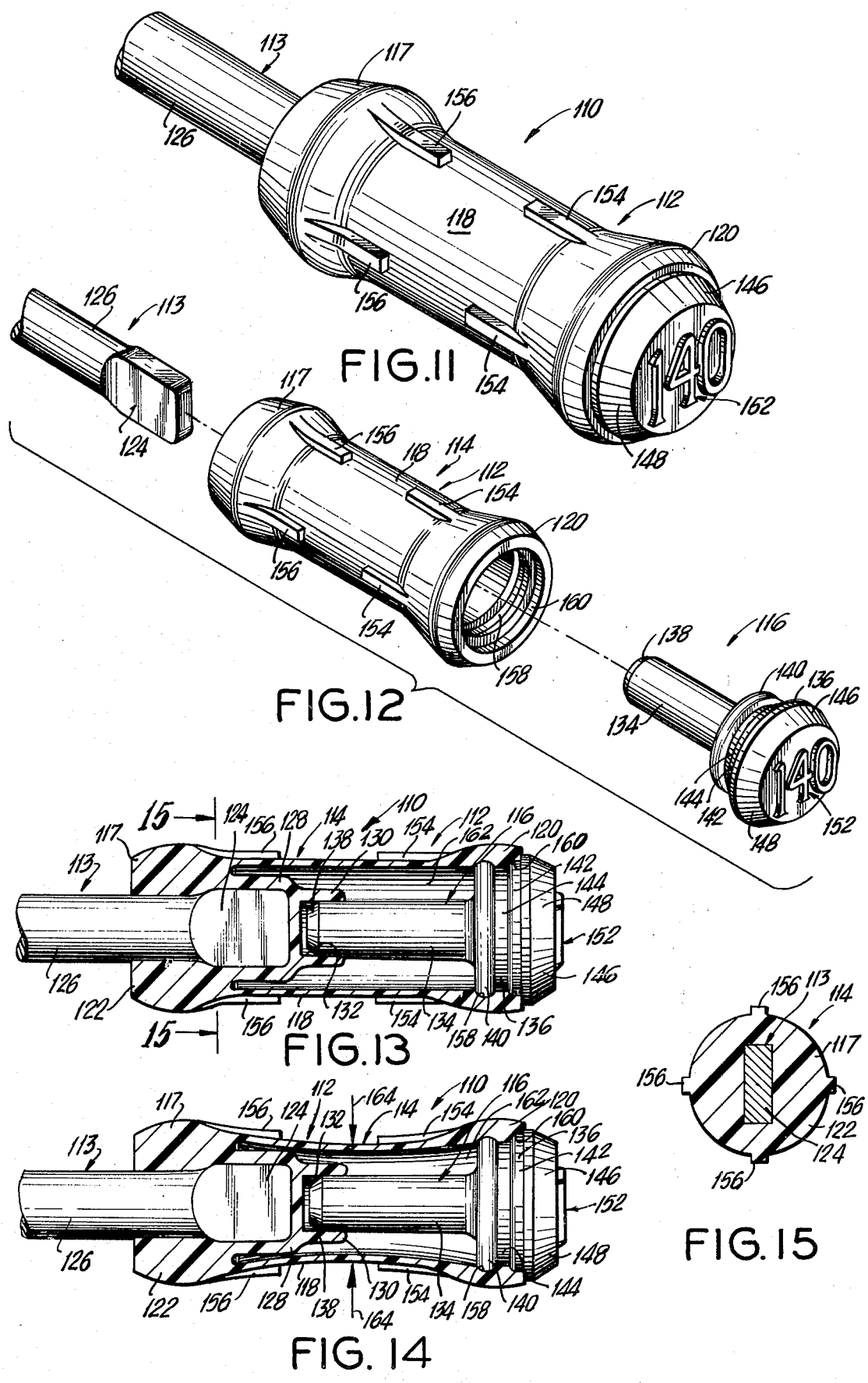

ENDODONTIC INSTRUMENT

BACKGROUND OF THE INVENTION

This invention relates to an endodontic instrument, and more particularly to a resilient handle which supports an endo blade of the type utilized for root canal therapy.

In root canal therapy, various instruments are needed for executing the procedure. These instruments include dental files, reamers, drill bits, and the like. Typically, these instruments, are all formed of wires or rods approximately 1 inch in length whose head is retained within a handle.

The different types of instruments and accessories required are usually part of a set of instruments, all of which have similar types of handles. Usually, the tools are identified by means of particular markings on the handle, such as a number and color code, which distinguish the different types of tools and their respective sizes, so that the dentist can select the proper instrument for use during the course of the root canal therapy.

In utilizing these instruments, the dentist holds the instrument handle between his fingers and continuously manipulates the handle by rotating it between his fingers, while at the same time the dentist axially reciprocates the instrument within the tooth. Such continuous manipulations utilizing the same two fingers of the dentist's hand is generally uncomfortable and painful and frequently may cause callouses to form on the fingers.

Accordingly, it is desirable to have a type of endodontic instrument for use in root canal therapy which provides more comfort to the user and avoids the inconvenience and pain during continuous working of the instrument.

SUMMARY OF THE INVENTION

It is accordingly an object of the present invention to provide an endodontic instrument of the aforementioned type which avoids the problems of prior art instruments.

A further object of the present invention is to provide an endodontic instrument for use in root canal therapy which includes a resilient handle.

Still another object of the present invention is to provide an endodontic instrument having a blade extending from one end of a handle, and wherein the handle is formed of resilient material for providing comfort to the user.

Yet a further object of the present invention is to provide an endodontic instrument having a resilient handle formed of two parts with the outer part flexibly riding over an inner part.

Another object of the present invention is to provide an endodontic instrument having a handle which can inwardly flex to provide resiliency during use.

Yet a further object of the present invention is to provide an endodontic instrument having a resilient handle formed of a central core with an outer sleeve flexibly disposed on the central core, and wherein an endo blade axially extends from either the core or the sleeve.

Briefly, in accordance with the present invention, there is provided an endodontic instrument having a handle and an endo blade extending from the front end of the handle. The handle is formed of two parts, specifically, a sleeve and a core, with the sleeve being formed of resilient material. The core is secured within the sleeve and includes a longitudinal body portion radially spaced from the inner walls of the sleeve to thereby define a flexure space between the core and the sleeve. The flexure space can accommodate the deformation of the sleeve upon gripping thereof during the use of the instrument.

The core can include an end cap which serves as a stop for the axial movement of the sleeve during deformation, or in a modified form, the end cap secures the end of the sleeve to the core. The end cap also accommodates a tool identification scheme. The handle can be color coded and a number can be placed on the end cap to identify the particular type and size of the tool.

In one embodiment of the invention, the front end of the sleeve is formed of solid material and the blade is encapsulated within the solid front end of the sleeve. In another embodiment, the core extends within the sleeve to the front of the handle and the blade is encapsulated within the core.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is a perspective view of the endodontic instrument in accordance with the present invention;

FIG. 2 is an exploded perspective view of a first embodiment of the instrument;

FIG. 3 is an elevational view of the handle of the instrument with the sleeve shown in cross-section, in accordance with the first embodiment of the present invention;

FIG. 4 is a sectional view taken along line 4—4 of FIG. 3;

FIG. 5 is a side sectional view similar to that shown in FIG. 3, showing the resilient deformation of the handle during gripping thereof;

FIG. 11 is a perspective view of a third embodiment of the instrument of the present invention;

FIG. 12 is an exploded perspective view of the third embodiment shown in FIG. 11;

FIG. 13 is an elevational view of the instrument shown in FIG. 11 with the sleeve shown in cross-section;

FIG. 14 is a side sectional view similar to that shown in FIG. 13, showing the resilient deformation of the handle during gripping thereof; and FIG. 15 is a sectional view taken along line 15—15 of FIG. 13.

In the various figures of the drawing, like reference characters designate like parts.

DETAILED DESCRIPTION OF THE PREFERRED EMBODIMENT

Figure 6:
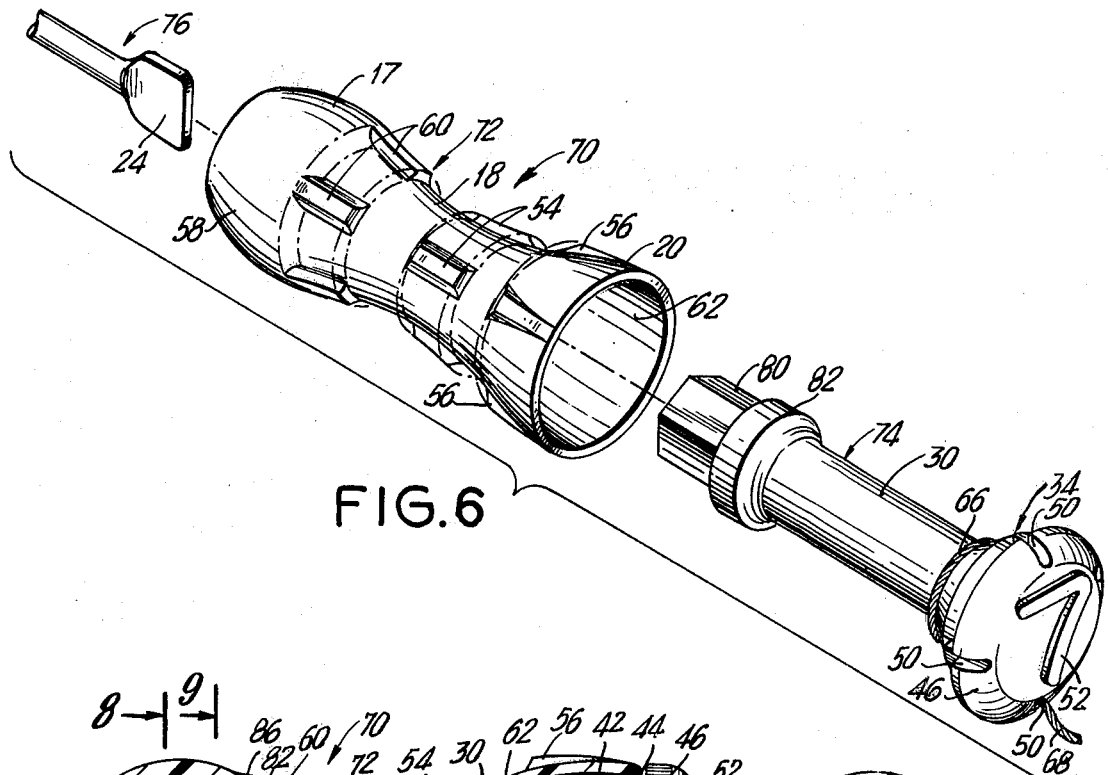
FIG. 6 is an exploded perspective view of a second embodiment of the instrument of the present invention.

Referring now to FIGS. 1-4, there is shown the endodontic instrument 10 having a handle 12 from which extends an endo blade 13 at its forward end. The term endo blade is used generically to describe all of the various types of conventional blades which can be used with such a handle 12 for use in root canal therapy, and includes dental files, reamers, drills, etc., wherein a showing of the various types of conventional blades is not thought necessary, these blades being well known in the art.

The handle 12 is formed of two parts, namely, a sleeve portion 14 and a central core portion 16. The sleeve portion 14 is formed in an hourglass shape and includes a forward end 17, a central section 18, and a tail end 20. The sleeve portion is circular in cross-section. The forward end 17 is formed of a solid material 22, typically a molded plastic material. As shown in FIGS. 3 and 4, an enlarged flat tang portion 24 of the blade 13, located at the head of the shaft portion 26, is embedded within the solid material 22 in the forward end 17 of the sleeve portion 14, so that the blade 13 cannot be pulled out of the sleeve portion 14, and so that the blade 13 rotates with the sleeve portion 14.

The central section 18 as well as the tail end 20 are hollow. A radially inwardly directed rib 28 is located within the hollow front portion of the central section 18 adjacent the forward solid end 22, the function of which will be set forth below.

The core portion 16 comprises a central cylindrical body section 30 separating a front end 32 and a rear end 34. The front end 32 includes a wider cylindrical head section having an annular groove 36 formed peripherally thereabout. A conical surface 38 separates the body section 30 from the head section 32. The forward end of the head section is also tapered at 40.

The rear end 34 includes a conical base 42 which terminates at its larger end in a cylindrical portion 44. A cap 46 is located against the cylindrical portion 44. The cap 46 has a periphery larger than the cylindrical portion 44 and accordingly provides a shoulder 48 thereto. Axial grooves 50 are provided through the cap 46 at its outer periphery. Preferably, four such grooves are shown. Additionally, a raised index number 52, such as the number "7" for example, is provided on the outer surface of the cap 46 for identifying the particular instrument and its size.

As can best be seen in FIG. 1, axially extending gripping ribs 54 are radially spaced apart from each other and are positioned around the periphery of the central section 18 of the sleeve portion 14. Stiffening and gripping ribs 56 are provided colinearly with the gripping ribs 54 and extend onto the tail end 20. The forward end 17 includes a raised surface 58 which terminates in stiffening and gripping ribs 60, also colinear with the gripping ribs 54. It should be noted, however, that the ribs 56 on the tail end 20 and the ribs 60 on the forward end 17 are axially spaced apart from the gripping ribs 54 to thereby provide two cylindrical portions on the central section 18 which are free from any ribs.

In assembling the instrument, the tang 24 of the blade 13 is directly molded within the forward end 17, and specifically within the solid material 22, as the sleeve portion 14 is being formed. After the sleeve portion is completed, the core portion 16 is secured within the sleeve portion 14 by inserting the core portion 16 into the sleeve portion 14 and snap fitting the sleeve internal rib 28 into the annular groove 36 of the core portion, as shown in FIG. 3. With the core portion so positioned within the sleeve portion, the tail end of the sleeve portion will lie on the cylindrical portion 44 at the rear end of the core portion. The cap 46 will be positioned exteriorly of the sleeve and the shoulder 48 will form a stop for the tail end of the sleeve portion.

With the core portion assembled within the sleeve portion, it should be noted that a peripheral space 62 is provided between the core portion and the inner wall of the sleeve portion. This space 62 defines a flexure space for accommodating deformation of the sleeve portion when gripping the handle 12 during use of the instrument.

Specifically, as shown in FIG. 5, when the instrument is being used, the handle 12 will be gripped at approximately its midsection with the gripping pressure, shown by the arrows 64, being applied onto the gripping ribs 54. The force resulting from this grip will deform the sleeve portion 14 and press the sleeve portion onto the body section 30 of the core portion 16. The tail end 20 of the sleeve portion will ride along the cylindrical portion 44 towards the conical base 42 of the core portion as the central section 18 deforms. By providing the discontinuities in the ribs 54, 56 and 60, specifically the cylindrical portions on each side of the ribs 54 which are free from ribs, the flexure of the sleeve will be facilitated.

Because of the resilient nature of the sleeve material, after the instrument is released, the sleeve portion will return to the initial position, as shown in FIG. 3, with the tail end 20 of the sleeve portion riding back from the conical base 42 along the cylindrical portion 44 until it reaches the shoulder stop 48 of the cap 46.

In order to prevent the instrument from dropping into the patient's mouth or falling onto the floor, a cord or string 66, such as dental floss material, is looped about the interconnection between the conical base 42 and the cylindrical body section 30 of the core portion. The string 66 is tightly fixed thereabout and extends through one of the axial grooves 50 within the cap 46 to pass out of the instrument to provide the string end 68. The string end 68 can then be attached to one of the dentist's fingers or to some other location, so that it can be prevented from falling down.

The sleeve portion can be made of molded nylon material and can be coded any color. The core portion can also be made of molded nylon material and color coded to identify the particular type of tool. The sleeve portion and/or the cap 46 of the core portion will then have the color desired and accordingly the particular tool will be easily identifiable by means of the color coded sleeve portion and/or cap. The raised number on the cap portion can also be used to identify the tool, such as to identify a particular size of the tool.

By means of the resilient nature of the sleeve material, and by permitting it to deform into the flexure space, there is effectively provided a softening of the handle to the dentist's touch. As the dentist continuously manipulates the tool by either rolling it and/or axially pulling it in and out, the deforming of the sleeve will provide more comfort and convenience for the dentist.

Referring now to FIGS. 6-10, a second embodiment of the present invention is shown. The endodontic instrument again includes a handle 70 provided with a sleeve portion 72 and a core portion 74, and an endo blade 76 extending from its forward end.

The sleeve portion 72 is substantially the same as in the previous embodiment with the exception that in the forward end 17, the solid material 22 includes an opening 78 therethrough in communication with the hollow space 62. The opening 78 is shaped to accommodate a front end 80 of the core portion 74 which extends therethrough. It is noted that the front end 80 is provided with a forward hexagonal portion, and accordingly the opening 78 will also be hexagonal, as best shown in FIG. 8, so that the core portion 74 rotates with the sleeve portion 72.

Figures 7, 8:
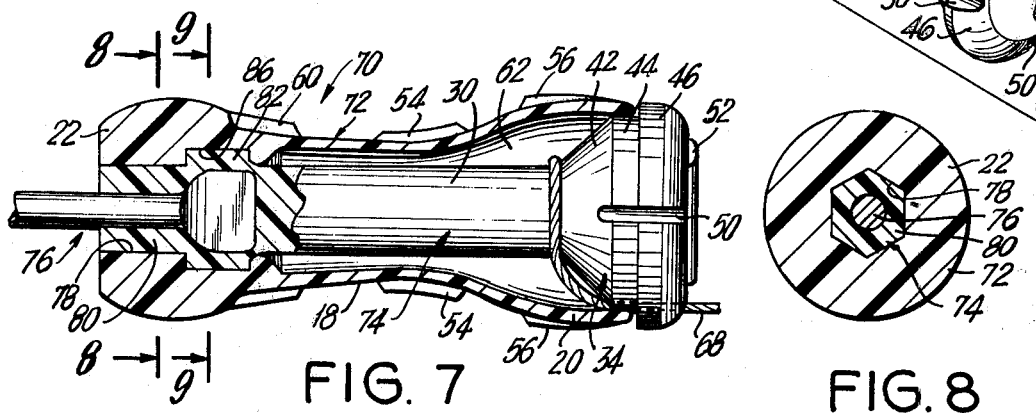
FIG. 7 is a side view of the embodiment shown in FIG. 6 with parts broken away and shown in section.
FIG. 8 is a cross-sectional view taken along lines 8—8 of FIG. 7.
Figures 9, 10:
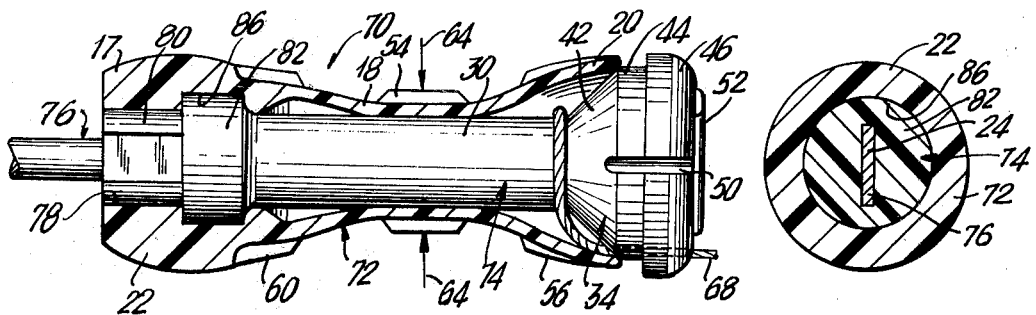
FIG. 9 is a cross-sectional view taken along line 9—9 of FIG. 7.
FIG. 10 is a side sectional view similar to that shown in FIG. 7, showing the resilient deformation of the sleeve as a result of gripping thereof during use of the instrument.

The enlarged tang 24 of the blade 76, as shown in FIGS. 7 and 9, is embedded into the front end 80 of the core portion 74, so that the blade 76 cannot be pulled out of the core portion 74, and so that the blade 76 rotates with the core portion 74 which in turn rotates with the sleeve portion 72, as set forth above.

The front end 80 also includes an outwardly directed cylindrical flange 82 which interconnects the forward hexagonal portion with the body section 30. This can best be seen in FIG. 6. The flange 82 is received within a circular recess 86 provided within the forward end 17 of the sleeve portion, as shown in FIGS. 7, 9 and 10, being snap fitted within the recess 86 to secure the sleeve and core portions together.

In the embodiment shown in FIGS. 6-10, it will be appreciated that the blade 76 is first embedded into the core portion during the molding of the core portion. Then, the blade and core portion are inserted together into the sleeve portion with the annular flange 82 being snap fitted within the recess 86 to hold the core portion and blade within the sleeve portion, wherein the hexagonal portion of the front end 80 is disposed in the hexagonal opening 78 to fix the position of the sleeve portion relative to the core portion With the embodiment shown in FIGS. 6-10, as the gripping pressure is applied, as shown by the arrows 64 in FIG. 10, the central section 18 of the sleeve portion will be resiliently deformed as the tail end 20 of the sleeve rides along the cylindrical portion 44 towards the conical base 42 of the core portion 74.

The other parts of the second embodiment now being described are substantially the same as those in connection with the first embodiment and are accordingly likewise numbered, wherein a further description of these same parts is not thought necessary.

Referring now to FIGS. 11-15, a third embodiment of the present invention is shown. The endodontic instrument 110 again includes a handle 112 from which extends an endo blade 113 at its forward end. The endo blade 113 is similar to the above mentioned endo blade 13, and again is used generically to describe all of the various types of conventional blades used in root canal therapy, wherein a showing of the various types of conventional blades is not thought necessary, these blades being well known in the art as set forth above.

The handle 112 is formed of two parts, namely, a sleeve portion 114 and a central core portion 116. The sleeve portion 114 is formed in an hourglass shape and includes a forward end 117, a central section 118, and a tail end 120. The sleeve portion is circular in cross-section. The forward end 117 is formed of a solid material 122, typically a molded plastic material. As shown in FIGS. 13-15, an enlarged flat tang portion 124 of the blade 113, located at the head of the shaft portion 126, is embedded within the solid material 122 in the forward end 117 of the sleeve portion 114, so that the blade 113 cannot be pulled out of the sleeve portion 114, and so that the blade 113 rotates with the sleeve portion 114.

The central section 118 as well as the tail end 120 are hollow. A stepped portion 128 projects inwardly from the forward end 117 to a position within the central section 118, the stepped portion 128 being radially spaced from the central section 118. The stepped forward end 130 of the projecting portion 128 is provided with a cylindrical opening 132 therein to provide a female member or receptacle within the sleeve portion 114, the function of which will be set forth below. It is noted, that the tang portion 124 of the blade 113 extends into the projecting stepped portion 128, as shown in FIGS. 13 and 14, to strengthen and reinforce the projecting stepped portion 128.

The core portion 116 includes a forward cylindrical body section 134 connected to a rear end 136. The forward end of the body section 134 is tapered at 138. The rear end 136 includes a cylindrical rib 140 connected to the core body section 134, and a spaced apart cylindrical portion 142 of approximately the same diameter to provide an annular groove 144 therebetween. A cap 146 is located against the cylindrical portion 142. The cap 146 has a periphery larger than the cylindrical portion 142 to provide a shoulder above the cylindrical portion 142. The side wall 146 of the cap 136 is tapered downwardly to the flat end surface 150 thereof. A raised index number 152, such as the number "140" for example, is provided on the end surface 150 for identifying the particular instrument and its size.

As best shown in FIGS. 11 and 12, radially spaced apart stiffening and gripping ribs 154 extend from the central section 118 onto the tail end 120. Additional radially spaced apart stiffening and gripping ribs 156 extend from the central section 118 onto the forward end 117. It is noted, that the ribs 154 and 156 are axially spaced apart from each other on the central section 118 to provide a cylindrical centrally located portion on the central section 118 which is free from any ribs.

In assembling the instrument 110, the tang 124 of the blade 113 is directly molded within the forward end 117, and specifically within the solid material 122, as the sleeve portion 114 is being formed, in the same manner mentioned above with respect to instrument 10. It is noted, that the internal surface of the tail end 20 of the sleeve is provided with an annular groove 158 and a stepped end 160. Thus, after the sleeve portion is completed to include the blade 113, the core portion 116 is secured within the sleeve portion 114 by first inserting the core body section 134 into the female opening 132 of the projecting portion 128 of the sleeve portion, wherein the tapered forward end 138 aids in this insertion.

Once the core portion 116 is initially inserted, the core portion 116 is centrally located with respect to the sleeve portion 114. The core portion 116 is now pushed further into the sleeve portion 114 so that the core rib 140 snaps into the sleeve groove 158, and the stepped sleeve portion 160 snaps into the core groove 144 and against the cylindrical core portion 142, as shown in FIGS. 13 and 14. The core cap 146 will now be positioned externally of the sleeve portion 114, wherein the cap shoulder forms a stop for the tail end 120 of the sleeve portion 114.

With the core portion assembled within the sleeve portion, it should be noted that a peripheral space 162 is provided between the core portion and the inner wall of the sleeve portion. This space 162 defines a flexure space for accommodating deformation of the sleeve portion when gripping the handle 112 during use of the instrument.

When the instrument 110 is being used, the handle 112 will be gripped at approximately its midsection with the gripping pressure being applied onto the sleeve portion 114 as shown by the arrows 164 in FIG. 5. The force resulting from this grip will deform the sleeve portion 114. By providing the discontinuities in the ribs 154, 156, specifically the cylindrical portion between the ribs, the flexure of the sleeve portion will be facilitated. It is noted, that the securement between the core body section 134 and the female portion 130 of the projecting stepped portion 128 of the sleeve portion provides a "floating connection" therebetween to accommodate any relative movement or displacement caused by the gripping pressure being applied onto the sleeve portion, thus facilitating the flexure of the sleeve portion shown in FIG. 14. After the instrument 110 is released, the sleeve portion will return to its initial position as shown in FIG. 13, due to the resilient nature of the sleeve portion material.

Here again, in order to prevent the instrument 110 from dropping into the patient's mouth or falling onto the floor, a cord or string such as dental floss material may be employed in the same manner mentioned above in either of the above two previously mentioned embodiments. Furthermore, the sleeve and core portions can be formed of the same material as mentioned above in the previous two embodiments, wherein these materials can be color coded to identify the particular type of tool.

Thus, the above three mentioned embodiments disclose instruments which effectively provide a soft handle to the dentist's touch, which is more comfortable and convenient for the dentist's use.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. An endodontic instrument comprising:
a handle;
a blade extending outwardly from a front end portion of said handle;
connecting means securing said blade in said front end portion of said handle for rotating said blade and said handle together;
said handle including an elongated sleeve member and a core member disposed within said sleeve member;
said sleeve member including a forward end and a tail end with a central section disposed between said forward and tail ends, said central section being hollow to provide a hollow interior therein, said tail end having an axial opening therethrough communicating with said hollow interior;
said core member including a longitudinal body portion having a head portion at one end and an enlarged base portion at an opposite end thereof;
said body portion being disposed in said hollow interior of said sleeve member with said body portion being radially spaced from inner walls of said sleeve member to define therebetween a flexure space for accommodating deformation of said sleeve member upon gripping thereof during use of the instrument;
engagement means for securing said head portion of said core member at said forward end of said sleeve member to prevent longitudinal movement between said head portion and said forward end;
said tail end of said sleeve member being free and resting on said base portion of said core member which is disposed within said axial opening of said tail end so that said tail end is free to ride along said base portion during said deformation of said sleeve member; and
said sleeve member including resilient means for permitting said central section to be radially inwardly deformed into said flexure space towards said core member.

2. An endodontic instrument as in claim 1, wherein said core member further includes an end cap on said base portion, said end cap extending beyond said sleeve member, said end cap having a radial dimension greater than said base portion for providing a shoulder stop for said tail end of said sleeve member.

3. An endodontic instrument as in claim 4, wherein said end cap further includes at least one axial passageway extending therethrough to accommodate passage of a string-like member which is looped around said body portion of said core member and is passed outwardly of said sleeve member through said axial passageway.

4. An endodontic instrument as in claim 1, wherein said head portion of said core member includes an annular groove, and said forward end of said sleeve member includes a radially inwardly directed rib for snap fitting into said annular groove to retain said core member within said sleeve member to define said engagement means.

5. An endodontic instrument as in claim 1, wherein said forward end of said sleeve member includes a circular recess and said head portion of said core member includes a radially outwardly extending flange for snap fitting into said recess to retain said core member within said sleeve member to define said engagement means.

6. An endodontic instrument as in claim 1, wherein said head portion of said core member is spaced from said front end portion of said handle, and wherein said blade includes a shaft and a securing tang at one end of said shaft, said securing tang being encapsulated within said front end portion of said handle to define said connecting means, said front end portion being a part of said forward end of said sleeve member.

7. An endodontic instrument as in claim 1, wherein said forward end of said sleeve member is provided with an axially oriented aperture therethrough for accommodating said head portion of said core member, said head portion of said core member terminating at a front end of said sleeve member, a part of said head portion and an associated part of said aperture having corresponding polygonal configurations, and wherein said blade includes a shaft and a securing tang at one end of said shaft, said securing tang being encapsulated within said head portion of said core member, said front end portion of said handle being a part of said head portion of said core member, said polygonal configurations of said associated parts of said head portion and said aperture causing said sleeve and core members to rotate together, and said encapsulated securing tang causing said core member and said blade to rotate together to define said connecting means.

8. An endodontic instrument as in claim 1, and further comprising axially extending gripping ribs radially spaced apart about an outer periphery of said central section of said sleeve member.

9. An endodontic instrument as in claim 1, wherein said core member is substantially non-compressible to limit depression of said sleeve member and to provide a longitudinal axial support for said handle.

10. An endodontic instrument as in claim 9, wherein said core member has a solid one piece construction.

11. An endodontic instrument as in claim 1, wherein said sleeve member includes an hourglass configuration defined by said forward end, central section and said tail end.

12. An endodontic instrument comprising:
a handle;
a blade extending outwardly from a front end portion of said handle;
connecting means securing said blade in said front end portion of said handle for rotating said blade and said handle together;
said handle including an elongated sleeve member and a core member disposed within said sleeve member;
said sleeve member including a forward end and a tail end with a central section disposed between said forward and tail ends, said central section being hollow to provide a hollow interior therein, said tail end having an axial opening therethrough communicating with said hollow interior;
said core member including a longitudinal body portion having a forward end portion and an enlarged base portion at an opposite end thereof;
said body portion being disposed in said hollow interior of said sleeve member with said body portion being radially spaced from inner walls of said sleeve member to define therebetween a flexure space for accommodating deformation of said sleeve member upon gripping thereof during use of the instrument;
engagement means for securing said base portion of said core member within said axial opening of said tail end of said sleeve member to prevent longitudinal movement between said base portion and said tail end;
said forward end of said sleeve member including floating connection means for securing said core member to permit longitudinal movement therebetween so that said sleeve member can be deformed radially towards said core member, said floating connection means including a receptacle provided on said forward end, said receptacle extending into said hollow interior, said forward end portion of said core member being longitudinally movably received in said receptacle; and
said sleeve member including resilient means for permitting said central section to be radially inwardly deformed into said flexure space towards said core member.

13. An endodontic instrument as in claim 12, wherein said sleeve member includes an hourglass configuration defined by said forward end, central section and said tail end.

14. An endodontic instrument as in claim 12, wherein said tail end of said sleeve member includes a circular recess and said base portion of said core member includes a radially outwardly extending rib for snap fitting into said recess to retain said core member within said sleeve member to define said engagement means.

15. An endodontic instrument as in claim 12, wherein said forward end portion of said core member is spaced from said front end portion of said handle, and wherein said blade includes a shaft and a securing tang at one end of said shaft, said securing tang being encapsulated within said front end portion of said handle to define said connecting means, said front end portion being a part of said forward end of said sleeve member.

16. An endodontic instrument as in claim 12, and further comprising axially extending gripping ribs radially spaced apart from an outer periphery of said central section of said sleeve member.

17. An endodontic instrument as in claim 12, wherein said core member is substantially non-compressible to limit depression of said sleeve member and to provide a longitudinal axial support for said handle.

18. An endodontic instrument as in claim 17, wherein said core member has a solid one piece construction.

* * * * *